US00PP28149P3

(12) United States Plant Patent
Mazzardis

(10) Patent No.: US PP28,149 P3
(45) Date of Patent: Jul. 4, 2017

(54) BLUEBERRY PLANT NAMED 'EB 9-2'

(50) Latin Name: ***Vaccinium* hybrid**
Varietal Denomination: EB 9-2

(71) Applicant: Vincent David Mazzardis, Joondalup (AU)

(72) Inventor: Vincent David Mazzardis, Joondalup (AU)

(73) Assignee: Bisa Trading Pty. Ltd., Cannington (AU)

( * ) Notice: Subject to any disclaimer, the term of this patent is extended or adjusted under 35 U.S.C. 154(b) by 24 days.

(21) Appl. No.: 14/756,610

(22) Filed: Sep. 24, 2015

(65) Prior Publication Data

US 2016/0113167 P1 Apr. 21, 2016

(30) Foreign Application Priority Data

Oct. 16, 2014 (AU) ..... PBR 2014/243

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

FOREIGN PATENT DOCUMENTS

AU 2014/243 10/2014

OTHER PUBLICATIONS

Plant Varieties Journal, vol. 28, Issue 1, Jun. 15, 2015.

*Primary Examiner* — Susan McCormick Ewoldt
(74) *Attorney, Agent, or Firm* — Randall Danskin P.S.

(57) ABSTRACT

A new and distinct variety of blueberry plant, which is denominated varietally as 'EB 9-2', and which produces a large, to very large fruit, and which further is mature for harvesting and shipment in the early season under the ecological conditions prevailing in Yanchep Springs, Western Australia.

1 Drawing Sheet

Latin name: '*Vaccinium* Hybrid'.

Varietal denomination: 'EB 9-2'.

RELATED APPLICATION DATA

The present application claims priority to Australian Plant Breeders Rights application Serial No. 2014/243, and which was filed one Oct. 16, 2014, and which was further accepted on Dec. 23, 2014.

BACKGROUND OF THE NEW VARIETY

The present invention relates to a new, novel and distinct variety of blueberry plant '*Vaccinium* hybrid' and which has been denominated varietally as 'EB 9-2'.

ORIGIN

The present variety of blueberry plant resulted from an ongoing development program which I have conducted to identify such plants. The purpose of this program is to improve the commercial quality of blueberry plants, and other species. To this end, I have made controlled hybrid cross-pollinations in order to produce plant populations from which improved progeny are evaluated, and thereafter selected.

The blueberry plant 'EB 9-2' was originated by me and selected from a population of new plants growing at my farm which is located near Yanchep Springs, in Yanchep, Western Australia. The new variety of blueberry plant was derived from a controlled cross-pollination of the seed parent, blueberry plant 'BB-1' [unpatented], and a pollen parent, blueberry plant '03-2' [unpatented], during the 2006 growing season. The seed parent, blueberry parent 'BB-1' is principally characterized by a semi-upright bush-type growing habit; a mid-season flowering date; and which further produces medium to large, firm, fruit. Still further, the pollen parent, blueberry plant '03-2' is principally characterized by a semi-upright growth habit; a mid-season flowering date; and which further produces large fruit. Following this cross-pollination, seed from the seed parent 'BB-1' produced approximately 500 plants. The first fruiting of these new plants was first observed in 2008. A complete assessment of the fruit, and growth habits of these new plants were evaluated in 2009. After this full assessment, the newly discovered variety 'EB 9-2' was selected for further asexual propagation and study. Further, asexual reproduction of the newly discovered variety 'EB 9-2' occurred during the 2010 through 2014 growing seasons. The subsequently conducted evaluations of the newly asexually propagated plants, and the fruit produced thereby, has lead the inventor to conclude that the newly discovered blueberry plant variety, 'EB 9-2', is a distinct, and new variety in view of its displayed upright, to semi-upright bush-type growth habit; large to very large and oblate shaped fruit; and which further has an excellent flavor; and a very early flowering, and fruit maturity dates in relative comparison to the closest known varieties. The asexual reproduction of this new and novel Blueberry plant named 'EB 9-2' occurred at Yanchep Springs, Western Australia.

In comparison to the seed parent 'BB-1', the present, newly discovery plant is clearly distinguishable therefrom based upon its flowering date. For example, the seed parent flowering date is considered mid-season under the ecological conditions prevailing in Yanchep Springs, Western Australia. On the other hand, the present, new variety has a date of flowering which is considered very early in the season. This is similarly the case with the pollen parent, blueberry plant '03-2', and which also has a mid-season flowering date. Still further, the new variety of blueberry plant is distinguishable from its seed parent in view of the fruit size produced by the new plant. In this regard, the new variety of blueberry plant produces large to very large fruit in relative comparison to the seed parent, and which produces only medium to large fruit; and the pollen parent which produces large sized blueberries.

The present, new and novel variety of blueberry plant is distinguishable from the most closely known variety, that being blueberry plant 'EB 8-1' which is further identified as U.S. Plant Pat. No. 25,859, and which was filed on Jun. 12, 2013 in view of the differing plant vigor; displayed growth habit; fruit bloom intensity; fruit firmness; fruit acidity; fruit weight, and other plant characteristics which will be discussed in the specification which follows. Still further, the new variety is clearly distinguishable from the common commercial blueberry plant variety 'Ridley 1111' which is further identified as U.S. Plant Pat. No. 23,572 and which was filed on Jan. 18, 2011. The blueberry plant variety 'Ridley 1111' produces medium to large sized fruit in comparison to the new variety of blueberry parent, and which produces large to very large fruit. It should be understood that the asexual propagation of the new, present variety of blueberry plant was accomplished by means of cuttings. The observations of the new and novel plants has taken place over a number of years and the inventor has repeatedly confirmed that the novel characteristics of the present, new variety of blueberry plant are stable across multiple generations.

BRIEF DESCRIPTION OF THE DRAWING

The accompanying drawing which is provided is a color photograph of the new blueberry plant 'EB 9-2', at an age of two (2) years, and which is juxtaposed relative to an image of the closest known variety, that being 'EB 8-1' (U.S. Plant Pat. No. 25,859). The photograph illustrates the new variety, and shows a portion of a vegetative stem which displays the growth habit of the leaves; one leaf is further illustrated showing the dorsal coloration thereof; and several fruit are depicted showing both the dorsal and ventral coloration, and the morphology of same. The photograph additionally shows a vegetative stem showing typical leaves and the fruit produced by the closest known variety, that being blueberry plant 'EB 8-1' (U.S. Plant Pat. No. 25,859).

The color in this photograph is as nearly true as is possible in a color representation of this type. Due to chemical development, processing, and printing, the leaves and fruit depicted in this photograph may or may not be accurate when compared to the actual specimens. For this reason, future color references should be made to the color plates, and descriptions provided hereinafter. Common color names are also employed in the specification which follows.

NOT A COMMERCIAL WARRANTY

The following detailed descriptions were prepared solely to comply with the provisions of 35 U.S.C. §112, and does not constitute a commercial warranty (either expressed or implied) that the present plant variety will, in the future, display the botanical, horticultural or other characteristics as set forth, hereinafter. Therefore, this disclosure may not be relied upon to support any future legal claims including, but not limited to, breach of warranty of merchantability, or fitness for any particular purpose, or non-infringement, which is directed, in whole, or in part, to the present new variety.

The colors and codes used herein to describe this new and novel Blueberry plant named 'EB 9-2', refer to The Royal Horticultural Society (R.H.S.) Colour Chart, 5$^{th}$ Ed., 2007.

The age of the plant at the time of the description that follows herein is three (3) years.

Plant:

*Plant vigor.*—Generally considered strong to very strong. This in contrast to the closest known variety 'EB 8-1' (U.S. Plant Pat. No. 25,859), and where this plant characteristic is merely considered medium or average.

*Plant growth habit.*—Considered upright to semi-upright. This in contrast to the closest known variety 'EB 8-1', and which displays a semi-spreading growth habit.

*Colour.*—One Year Old Shoots — Yellow Green 144C (R.H.S. Colour Chart, 5$^{th\ Ed.,}$ 2007). This color is virtually indistinguishable from the same plant characteristic as expressed by the closest known variety 'EB 8-1'.

*Internode length.*—One Year Old Shoots — about 22 mm; and are considered long to very long for the species. This is in contrast to the same growth habit as expressed by the closest known variety 'EB 8-1', and which displays a medium to long internode length. Height of plant at time of description is about 1.3 m. Width of plant at time of description is about 1.2 m.

*Bark color.*—Greyed Orange 177B (R.H.S. Colour Chart, 5$^{th}$ Ed., 2007).

*Leaf length.*—Considered short to average in length, about 62 millimeters. This in contrast to the closest known variety 'EB 8-1', and which has a medium to long leaf length of about 63.17 millimeters.

*Leaf width.*—Considered narrow to medium in width, about 31 millimeters. This is in contrast to that same displayed plant characteristic of the closest known variety 'EB 8-1', and which is considered medium to broad in width, and which further has a displayed width, on average, of about 29.6 millimeters.

*Leaf.*—Ratio of Length Versus Width — Considered large for the species. This is in contrast to that characteristic displayed by the closest known variety 'EB 8-1' and which is only considered medium to large.

*Leaf shape.*—Considered ovate.

*Leaf colour.*—Dorsal surface — Yellow Green 148C (R.H.S. Colour Chart, 5$^{th}$ Ed., 2007).

*Leaf color.*—Under Surface — Yellow Green 148C (R.H.S. Colour Chart, 5th Ed., 2007).

*Texture of the leaf.*—Glabrous.

*Leaf apex shape.*—Acute.

*Leaf apex base shape.*—Rounded.

*Vein color of the leaf.*—Yellow Green N144C (R.H.S. Colour Chart, 5th Ed., 2007).

*Venation pattern of the leaf.*—Pinnately reticulate.

*Leaf arrangement.*—Alternate.

*Leaf color.*—Intensity — The dorsal surface color intensity is considered average for the species.

*Leaf marginal edge.*—Entire.

Flowers:

*Flower bud coloration.*—The anthocyanin coloration is considered very weak.

*Inflorescence.*—Length — about 26.5 mm. Considered average for the species.

*Color of opened flower.*—White NN155C (R.H.S. Colour Chart, 5th Ed., 2007).

*Average number of flowers per inflorescence is.*—4-5.

*Corolla texture.*—Rigid.

*Corolla length.*—About 9.5 mm.

*Corolla diameter.*—About 10 mm.

*Corolla color.*—White NN155B (R.H.S. Colour Chart, 5th Ed., 2007).

*Corolla aperture size.*—About 4.4 mm.

*Pedicle length.*—About 5.4 mm.

*Pedicle color.*—Yellow Green 150C (R.H.S. Colour Chart, 5th Ed., 2007).

*Flower.*—Corolla Shape — Urceolate.

*Flower.*—Corolla Tube Size — Considered medium.

*Corolla tube coloration.*—The anthocyanin coloration is considered absent or very weak.

*Corolla tube surface texture.*—Ridges are present.

*Seed color.*—Greyed Orange 168C (R.H.S. Colour Chart, 5th Ed., 2007).

Fruit:

*Fruit cluster density.*—Generally considered average to dense. This is in contrast to the blueberry variety 'EB 8-1', and where this plant displays an average fruit cluster density.

*Unripe fruit coloration.*—Yellow Green 144B (R.H.S. Colour Chart, 5th Ed., 2007). Considered a light to medium green.

*Fruit size.*—Considered large to very large for the species. This is in contrast to the closest known variety 'EB 8-1', and where the fruit is considered just merely large.

*Fruit shape.*—Generally speaking, and when viewed in a longitudinal sectional view, the fruit shape is considered oblate.

*Fruit sepal orientation.*—Generally speaking, the sepals are considered erect to semi-erect.

*Sepal type.*—Generally considered reflexed. This is in contrast to the closest known variety 'EB 8-1', and where the same displayed plant characteristic is considered straight.

*Calyx basin diameter.*—Considered average for the species, about 9.60 mm. This is in contrast to the closest known variety 'EB 8-1', and where the same displayed plant characteristic is considered medium to large.

*Calyx basin depth.*—Considered average, about 2.97 mm.

*Intensity of fruit bloom.*—Considered very strong in contrast to the closest known variety 'EB 8-1', and which is only considered merely strong for the variety.

*Fruit skin coloration.*—Black 203C (R.H.S. Colour Chart, 5th Ed., 2007).

*Fruit flesh color (ripened fruit).*—Yellow Green 145C (R.H.S. Colour Chart, 5th Ed., 2007).

*Fruit firmness.*—The fruit produced by the new variety is considered to be firm to very firm for the species. This is in contrast to the closest known variety 'EB 8-1', and where this displayed fruit firmness is considered merely average.

*Fruit sweetness.*—Considered high for the variety. This is in contrast to the closest known variety 'EB 8-1', and which is considered merely average.

*Fruit acidity.*—Generally — Considered low to medium for the species. This is in contrast to the closest known variety 'EB 8-1', and which is considered to be merely average.

*Fruiting type.*—Fruiting occurs on one year old, and current season's shoots.

*Time of vegetative bud burst.*—Not applicable as Blueberry Plant EB 9-2 is an Evergreen.

*Time of flowering.*—First bloom is about February-March in the specified location of culture, and the second bloom is about June-July in the specified location of culture.

*Time of flowering.*—On current year's shoots — Considered very early in the season for the species in the specified location of culture.

*Time of fruit ripening on one year old shoots.*—Considered very early in the season for the species in the specified location of culture.

*Time of fruit ripening on current year shoots.*—Considered very early in the season for the species in the specified location of culture.

*Fruit diameter.*—About 21.62 millimeters, on average.

*Fruit height.*—Generally about 15.43 millimeters, on average.

*Fruit weight.*—About 4.79 grams, on average. Storability of the plant fruit is considered to be long.

Reproduction organs of the plant:

*Size of the pollen anthers.*—About 5.5 mm.

*Color of the pollen anthers.*—Greyed Orange 163D (R.H.S. Colour Chart, 5th Ed., 2007).

*Pistil length.*—About 6.5 mm.

*Pistil color.*—Yellow Green 144C (R.H.S. Colour Chart, 5th Ed., 2007). Market use of the fruit is First Grade Fresh Market Fruit.

*Pollination requirement.*—Self-fertile. The observed date of the first pick of the first bloom is approximately March in the specified location of culture. The observed date of the last pick of the second bloom is approximately December in the specified location of culture.

*Resistance to insects and disease.*—No particular susceptibilities were noted. The present variety has not been tested to expose or detect any susceptibilities or resistances to any known plants and/or fruit diseases.

Although the new variety of blueberry plant named EB 9-2 described herein possesses the described characteristics when grown under the ecological conditions prevailing near Yanchep Springs, Western Australia, it should be understood that variations of the usual magnitude and characteristics incident to changes in growing conditions, fertilization, pruning, pest control, frost, climatic variables and horticultural management are to be expected.

Having thus described and illustrated my new variety of blueberry plant, what I claim is new and desire to secure by plant Letters Patent is:

1. A new and distinct variety of blueberry plant, substantially as illustrated and described, and which is characterized as to novelty by producing a large to very large fruit, and which further is mature for harvesting and shipment in the very early season under the ecological conditions prevailing near Yanchep Springs, Western Australia.

* * * * *

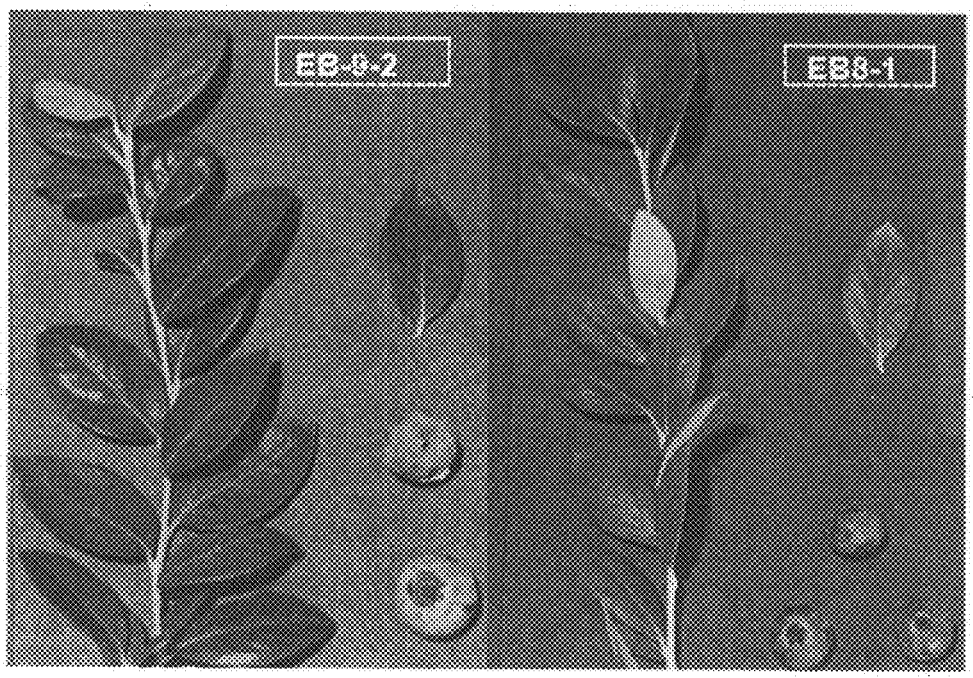
EB-9-2
EB8-1